United States Patent [19]

Horiuchi et al.

[11] Patent Number: 4,816,350

[45] Date of Patent: Mar. 28, 1989

[54] GRADIENT RADIATION IMAGE CONVERSION SHEET

[75] Inventors: Hidenaga Horiuchi, Kanagawa; Hisao Suzuki; Yuji Aoki, both of Odawara; Norio Miura, Isehara, all of Japan

[73] Assignee: Kasei Optonix Ltd., Tokyo, Japan

[21] Appl. No.: 7,405

[22] Filed: Jan. 27, 1987

[30] Foreign Application Priority Data

| | | | |
|---|---|---|---|
| Jan. 24, 1986 | [JP] | Japan | 61-13284 |
| Feb. 28, 1986 | [JP] | Japan | 61-43634 |
| Apr. 9, 1986 | [JP] | Japan | 61-81449 |

[51] Int. Cl.[4] .......... G21K 4/00; A61B 6/00

[52] U.S. Cl. .......... 428/690; 428/691; 428/917; 250/483.1; 250/484.1; 250/487.1

[58] Field of Search .......... 428/690, 691, 917; 250/483.1–488.1

[56] References Cited

U.S. PATENT DOCUMENTS

| | | | |
|---|---|---|---|
| 2,820,146 | 1/1958 | Kunes | 250/487.1 |
| 3,665,191 | 5/1972 | Moody | 250/3.68 |
| 4,362,944 | 12/1982 | Suzuki et al. | 250/483.1 |
| 4,368,390 | 1/1983 | Takahashi et al. | 250/363 |

FOREIGN PATENT DOCUMENTS

| | | |
|---|---|---|
| 0021174 | 1/1981 | European Pat. Off. . |
| 0158862 | 10/1985 | European Pat. Off. . |
| 2327126 | 12/1974 | Fed. Rep. of Germany . |
| 3031267 | 6/1984 | Fed. Rep. of Germany . |
| 10425 | 5/1960 | Japan . |
| 73400 | 6/1981 | Japan . |

*Primary Examiner*—Nancy A. B. Swisher

*Attorney, Agent, or Firm*—Oblon, Fisher, Spivak, McClelland & Maier

[57] ABSTRACT

A gradient radiation image conversion sheet, comprising a protective layer a fluorescent layer and a support layer, and the transmissions of said protective layer and/or said fluorescent layer are partially changed and the dots of the print of said gradient patterns and the border between the printed area and the unprinted area are blurred. The gradient image conversion sheet has a gradation area in which the change in transmission is extremely smooth and a speed ratio which may be set in a relatively wide range, and the sheet can be produced through a mass-production system to give products of constant quality.

12 Claims, 1 Drawing Sheet

GRADIENT RADIATION IMAGE CONVERSION SHEET

BACKGROUND OF THE INVENTION

1. Field of the Invention

The present invention relates to a radiation image conversion sheet, and more particularly to a gradient radiation image conversion sheet.

2. Prior Art

The radiation image conversion sheet (hereinafter referred to simply as "image conversion sheet") has hitherto been used in various fields of art including a medical field, where it is used for radiography for medical diagnosis or other medical purposes such as direct radiography, photofluorography or fluoroscopy, and industrial applications where it is used for non-destructive inspection of various materials, while contacting close to an X-ray photograph film (hereinafter referred to simply as "film") to improve the sensitivity of the photographing system. Alternatively, the X-ray is converted into a visible ray thereby and then the thus converted visible ray is photographed on a film. Principally, such an image conversion sheet includes a support, such as paper or plastic materials, and a fluorescent layer disposed on one side thereof. The fluorescent layer is composed of a phosphor for emitting high luminance light upon irradiation with a radiation, and a binder resin in which the phosphor is dispersed. In general, the surface of the fluorescent layer (i.e. the surface opposed to the side on which the support is applied) is protected by a transparent protective layer made of, for example, cellulose acetate, cellulose acetate butylate, polymethyl methacrylate or polyethylene terephthalate. There has also been known in the art an image conversion sheet in which a light reflecting layer or a light absorbing layer is disposed between the support and the fluorecent layer. In radiographic operation, the image conversion sheet is placed closely over the film so that the fluorescent layer faces to the film through the transparent protective layer. It is a common practice that two image conversion sheets are contacted closely on both side faces of the film, and the film sandwitched by the two image conversion sheets is held in a frame, a so-called "cassette", ready for photographing.

The method using the combination of an image conversion sheet and a radiophographic film having an emulsion layer composed of a silver salt photosensitive material for forming a radiographic image is referred to as radiophotography. In recent years, there is a demand for a method capable of forming a radiographical image without using a silver salt, in view of the shortage of silver resource.

As one proposal of the radiation image conversion method wherein no silver salt is used, a radiation image conversion panel comprising a stimulable phosphor has been proposed by U.S. Pat. No. 3,859,527. In this connection, the stimulable phosphor means a phosphor which emits light upon irradiation with a radiotion ray followed by irradiation with an electromagnetic wave selected from visible and infrared rays, the radiotions including electromagnetic wave or particle ray such as X-ray, alpha-ray, beta-ray, gamma-ray, high energy neutron ray, electron ray, vacuum ultraviolet ray or ultraviolet ray. In this known method, the radiotion ray passed through the object to be photographed is absorbed by a stimulable phosphor in the panel, and then the panel is scanned with an electromagnetic wave (acting as a stimulating ray) selected from visible and infrared rays to pick up the radiographical image as a time sequence of stimulated lights which are electrically processed to form an image.

On the other hand, in diagnosis of thoracic diseases, such as lungs cancer, by the use of chest X-ray radiography, it becomes necessary increasingly to observe the trachea and bronchi overlapping or interlocked complicately with each other in the thoracic vertebra and heart in addition to the observation of the photograph of the lung field for correct and precise diagnosis. However, an ordinary image conversion sheet generally has an even sensitivity throughout the overall area thereof so that the fluorescent light intensity of the light emitted from the fluorescent layer irradiated with X-ray is substantially constant over the entire area, and the film has a constant sensitivity throughout the entire surface area thereof. When the chest of a patient is observed through a simple radiography or a tomography, it becomes difficult to inspect or observe the lung field and simultaneously the interlocked trachea and bronchus in the thoracic vertebra and heart from single sheet of X-ray photograph. In detail, various organs in the chest have individual transmission factors to X-ray which are different from each other in a wide range, so that the film densities of the thoracic vertebra, heart and lung field become denser in this order to distribute in a relatively wide range. Accordingly, when photography is conducted under an X-ray exposure condition optimum for obtaining the film density suited for observation of the lung field, the film densities of the thoracic vertebra and heart becomes too low due to absorption of X-ray by these organs, leading to the result that the trachea and bronchus overlapped with these organs are not photographed to make it impossible to inspect the trachea and bronchus. Conversely, when radiography is conducted under an X-ray exposure condition for obtaining a film density suited for inspection of the trachea and bronchus, the density of the lung field image becomes excessively high for inspection of the lung field.

Under these circumstances, it has been a common practice to photograph plural X-ray photographs under X-ray exposure conditions suited respectively for obtaining photographs of the lung field and of the trachea and bronchus to have the images thereof having proper densities, or the X-ray photograph of the chest has been inspected together with the result of bronchography conduced by the use of a contrast medium to make a diagnosis of the diseases in the chest. However, it is not preferred to have plural X-ray photographs since the exposure dose to the patient is increased, and the X-ray bronchography suffers the patient a severe pain and has additional problems that it cost times and expenses amounting to several times as much as those required for a simple photography.

In order to solve the aforementioned problems, proposals have been made to use an image conversion sheet, i.e. a gradient image conversion sheet, with a speed partially varied. The gradient image conversion sheets of preceding proposals include, a type wherein the thickness of the fluorescent layer is partially varied to effect gradation in speed or sensitivity, a type wherein a light reflecting layer containing a white pigment or the like is dispersed at localized portions between the support and the fluorescent layer to improve the sensitivity of the portion provided with the light reflecting layer to achieve the aimed gradation, a type using phosphors having different luminance so that the speed is complemented, and a type wherein a light absorbing layer composed of a coloring agent having a body color, such as black, blue or red, is introduced at desired portion of the interface between the support and the fluorescent layer to lower the speed of the portion provided with such a coloring agent.

However, the gradient image conversion sheets of the known types tend to give clear border lines between the high speed portions and the low speed portions due to the caused inherent to the technology for preparing the same, and thus there appear border or marginal areas of the gradient region on the the X-ray photograph boarder regions in which the photographing speeds are abruptly changed to provide adverse influences on diagnosis. The known type gradient image conversion sheets have further disadvantages that it is hard to produce the products satisfying the desired requirements or specifications, and that it is not easy to produce products of uniform quality by mass production.

As another proposal for solving the aforementioned problems, Japanese Utility Model Publication No. 19425/1980 discloses a system in which the speed or sensitivity is varied by the use of a printed card board. However, even if the card board is printed with a gradation printing of ordinary type, there appears a clear image of the border between the portion bearing the printing of lightest shade and the unprinted portion to provide inconvenience for clinical application. A still further proposal has been made by Unexamined Japanese Patent Publication No. 161900/1983 to eliminate the inconvenience of clear distinctive imaging of the border between the printed and unprinted regions. However, the highest compensation in speed or sensitivity accomplished by this prior proposal is only about 2 times, with attendant disadvantages that it is required to print for two or more times, and that various problems relating to color scheme or printing positions are involved therein.

OBJECTS AND SUMMARY OF THE INVENTION

Accordingly, a primary object of this invention is provide a gradient image conversion sheet by which a desired compensation in speed or sensitivity can be easily realized. Another object of this invention is to provide such a gradient image conversion sheet which can be produced through a mass-production system to give products of constant quality.

A more specific object of this invention is to provide a gradient image conversion sheet having a gradation area in which the change in transmission is extremely smooth.

A further specific object of this invention is to provide such a gradient image conversion sheet having a speed ratio which may be set in a relatively wide range.

With the aforementioned objects in view, a first embodiment of the invention resides in a gradient radiation image conversion sheet, comprising a protective layer carrying gradient patterns printed with a gradient patterns printing ink containing a resin and/or colorant, a fluorescent layer formed by applying on said protective layer with a coating dispersion of a phosphor, said coating dispersion containing, in addition to said phosphor, a solvent for said resin and/or said colorant in said ink so that said resin and/or said colorant are dispersed or bled into said protective layer and/or said coating dispersion of said phosphor, and a support layer disposed on said fluorescent layer, whereby the transmissions of said protective layer and/or said fluorescent layer are partially changed and the dots of the print of said gradient patterns and the border between the printed area and the unprinted area are blurred.

A second embodiment of the invention resides in a gradient radiation image conversion sheet, comprising a support layer carrying gradient patterns printed with a gradient patterns printing ink containing a resin and/or colorant, a fluorescent layer formed by applying on said support layer with a coating dispersion of a phosphor, said coating dispersion containing, in addition to said phosphor, a solvent for said resin and/or said colorant in said ink so that said resin and/or said colorant are dispersed or bled into said coating dispersion of said phosphor, and a protective layer disposed on said fluorescent layer, whereby the transmissions of said protective layer and/or said fluorescent layer are partially changed and the dots of the print of said gradient patterns and the border between the printed area and the unprinted area are blurred.

A third embodiment of the invention resides in a gradient radiation image conversion sheet, comprising a support layer, a fluorescent layer disposed on said support layer, said fluorescent layer carrying gradient patterns printed with a gradient pattern printing ink containing a resin and/or a colorant, and a protective layer formed by applying on said fluorescent layer with a resin solution containing, a solvent for said resin and/or said colorant in said ink and a protective layer forming resin so that said resin and/or said colorant are dispsersed or bled into said fluorescent layer and/or said coating dispersion whereby the transmissions of said protective layer and/or said fluorescent layer are partially changed and the dots of the print of said gradient patterns and the border between the printed area and the unprinted area are blurred.

A fourth embodiment of the invention resides in a gradient radiation image conversion sheet, comprising a protective layer formed by applying on a base plate, a base plate carrying gradient patterns printed with a gradient patterns printing ink containing a resin and/or colorant, with a resin solution containing, a protective layer forming resin and a solvent for said resin and/or said colorant in said ink so that said resin and/or said colorant are dispersed or bled into said coating dispersion, a fluorescent layer disposed on said protective layer, and a support layer disposed on said fluorescent layer, whereby the transmissions of said protective layer and/or said fluorescent layer are partially changed and the dots of the print of said gradient patterns and the border between the printed area and the unprinted area is blurred.

DESCRIPTION OF THE DRAWING

The above and other objects and advantages of this invention will become apparent from the following detailed description thereof with reference to the appended drawing, in which.

DESCRIPTION OF THE INVENTION

Figure 1:
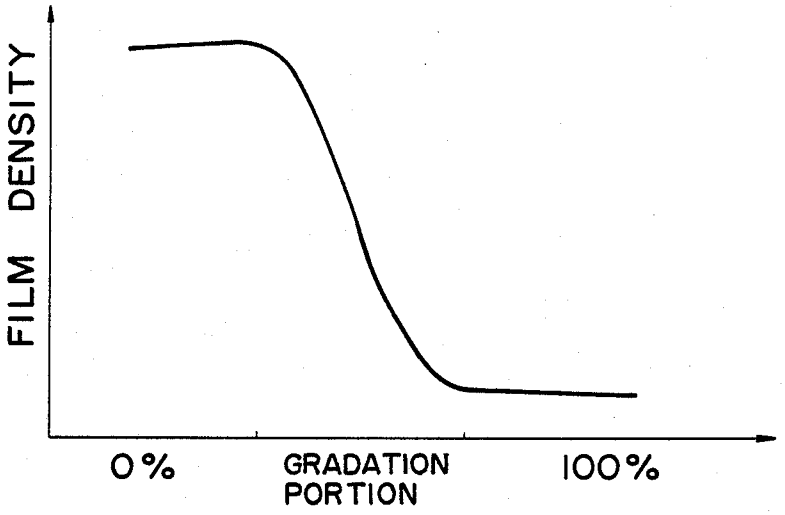
FIG. 1 is a graphic representation of an X-ray film density obtained by the use of an embodiment of the gradient image conversion sheet according to the present invention.

The "support" used in this invention may be made of any proper material. Preferred examples are: various paper sheets and paper base sheets covered with various polymeric materials such as polyethylene; metal foil such as an aluminium foil, and foil-paper laminates; various plastics films such as a film formed of cellulose acetate, cellulose propionate, cellulose acetate butylate, polystyrene, polymethylmethacrylate, vinyl chloride/-vinyl acetate copolymers or polyethylene terephthalate; and a glass plate.

The thickness of the support generally ranges about 300 to 400 microns for paper base supports and about 100 to 300 microns for plastics base films, and the material for and the thickness of the support may be selected in consideration of the applied uses.

Any of the known phosphors used conventionally in image conversion sheets of normal type may be used without any modification. Preferred phosphors include those which emit spontaneous luminescence of high luminance upon irradiation with radiation and generally used in the radiophotography, the specific examples being $CaWO_4$; $BaSO_4$:Pb; (Cd,Zn)S:Ag; $Gd_2O_2S$:Tb; $La_2O_2S$:Tb, etc. As the examples of stimulable phosphors which may be used in the radiation image conversion method wherein no silver salt is used, it may be mentioned to SrS:Ce,Sm; SrS:Eu,Sm; BaFBr:Eu, etc. These phosphors may be preferably used in the form of particles each having a particle size of from about 1 to 30 microns.

The coating dispersion of phosphor for forming the fluorescent layer is comprised of any one or more of said phosphor, a solvent and a resin. Examples of usable resins are nitrocellulose, cellulose acetate, ethyl cellulose, polyvinyl butyral, vinyl chloride/vinyl acetate copolymers, polycarbonate, polymethyl methacrylate and polyurethane.

The solvent dissolves the resin and/or the colorant contained in the gradient patterns printing ink, as will be described in detail hereinafter, in the first and second embodiments. It is preferred that the solvent should have the following properties.

(a) It should have a proper dissolution or dilution power for the resin and/or the colorant used in the ink, and a desired evaporation rate.

(b) It should not affect adversely on the colorant (dye or pigment) used in the ink so as not to cause crystal transition (change in hue, depression in coloring power) or agglomeration (solvent shock, color segregation, sedimentation or depression of coloring power).

Examples of preferred solvents are: aliphatic hydrocarbons such as mineral spirit, petroleum naphtha, etc.; aromatic hydrocarbons such as toluene, xylene, etc.; alcohols such as ethyl alcohol, isopropyl alcohol, butyl alcohol, etc.; ketones such as acetone, diisobutyl ketone, diethyl ketone, methyl ethyl ketone, etc.; esters such as acetate esters, butylate ester, etc.; and ethers such as isopropyl ether, ethyl ether, cellosolve diethyl, etc. In view of the empirical rule that "a compound is well soluble in like compounds", it is preferable to select a solvent having a solubility parameter close to that of the resin used in the ink.

However, in the third and fourth embodiments of this invention, the selection of the solvent in the resin solution for forming a protective layer is not critical and thus the usable solvent is not limited to the aforementioned solvents as far as it can dissolve the resin used in the ink.

The fluorescent layer formed by the use of the coating dispersion for forming the aforementioned fluorescent layer has a thickness generally ranging from about 100 to about 300 microns. It is preferred that the weight ratio of the phosphor to the resin (solid base) is in the range such that 2 to 20 parts by weight of the resin is present per 100 parts by weight of the phosphor.

A variety of commercially available plastics films may be used directly as the "protective layer" in this invention, or the protective layer may be formed by using a variety of resin solutions.

Examples of plastics films, which may be used as forming the protective layer without any processing, are 4 to 12 micron thick transparent films of polycarbonate, polymethyl methacrylate or polyethylene terephthalate.

On the other hand, the resin solution is prepared by dissolving a selected resin in a solvent. As preferred examples of such resin, it may be mentioned to cellulose acetate butylate, cellulose acetate, polyvinyl butyral, vinyl chloride/vinyl acetate copolymers, polymethyl methacrylate and polyurethane. The solvent is not critical, and any desired solvent may be used as far as it dissolves the selected resin. However, in the third and fourth embodiments, the solvent used for the preparation of the resin solution should disolve the resin and/or the colorant contained in the gradient pattern printing ink. Examples of such a solvent are those referred to hereinbefore as the solvent used in preparation of the coating dispersion of the phosphor for forming the fluorescent layer.

It is preferred that the thickness of the protective layer formed by using the resin solution ranges from about 3 to about 30 microns.

Any of the commercially available printing inks may be directly used as the "gradient pattern printing ink", as long as it contains a resin and/or a colorant which is soluble in the solvent used for the preparation of the dispersion coating of phosphor for forming the fluorescent layer or soluble in the solvent used for the preparation of the resin solution for forming the protective layer. Particularly preferred are drying evaporation type inks; and specific examples of the resin used in the printing ink are natural resins such as rosin, shellac, copal, dammar, gilsonite, etc.; derivatives of natural resins such as setting rosin, maleic resins, fumarate resins, etc.; and synthetic resins such as phenol resins, xylene resins, ketone resins, petroleum resins, terpene resins, chlorinated rubbers, alkyd resins, polyamide resins, acrylic resins, polyvinyl chloride, polyvinyl chlorideacetate; and derivatives of cellulose, such as nitrocellulose, acetylcellulose, cellulose acetate butyrate, etc.

Particularly when only the colorant in the "gradient pattern printing ink" is bled by the solvent used in the resin solution for forming the protective layer or by the solvent used in the coating dispersion for forming the fluorescent layer while the resin fraction being not bled, it is preferred to use an ink containing the same series resin as that for forming the fluorescent layer or the protective layer, in view of the solubilities or dispersibilities of the resins. Accordingly, when the used solvent is an esteric solvent (e.g. butyl acetate), it is preferred to use, as the resin in the printing ink, cellulose acetate, polyvinyl butyral (e.g. BM-1, BM-2, BM-5, BL-1, BL-2, BH-3 and BX-L, all being produced by Sekisui Chemical Co., Ltd.) polyurethane resins, epoxy resins and UV curing resins. When an alcoholic solvent (e.g. ethyl alcohol) is used, it is preferred, as the resin contained in the printing ink, to use a polyester resin, cellulose acetate, an acrylic resin, polyvinyl chloride-acetate, a polyurethane resin, an epoxy resin or a UV curing resin. When an aromatic solvent (e.g. toluene) is used, it is preferred to use, as the resin contained in the printing ink, cellulose acetate, polyvinyl butyral, BL-1, BL-2, BM-1, BM-2, BM-5, BL-3, BX-1, BX-7, BY-3 and BY-4, all being produced by Sekisui Chemical Co., Ltd.), vinyl chloride-acetate, nitrocellulose or cellulose acetate.

On the other hand, as the colorant contained in the printing ink, usable are any of oil-soluble dyes, disperse dyes, organic pigments and inorganic pigments, as far as they are soluble or dispersible in the vehicles for the ink, and it is more preferable to use a dye or a pigment which is soluble in the coating dispersion for forming the fluorescent layer or the resin solution for forming the protection layer, the typical examples being oil-soluble dyes. In order to have an increased speed ratio, it is more preferable to use a yellow series dye having an absoption band near 420 μm when $CaWO_4$ is used as the phosphor, and it is more preferable to use a red series dye having an aborption band near 550 μm when $Gd_2O_2S$:Tb is used as the phosphor.

In order to further smoothen the change in transmission within the gradation region in the gradient image conversion sheet, according to this invention, it is particularly preferable to use a "gradient pattern printing ink" containing a particular combination of components so that the resin contained therein is not soluble but only the colorant therein is soluble in the coating dispersion for forming the fluorescent layer or the resin solution for forming the protective layer.

The "gradient pattern" is not critical, and any of the known patterns may be properly selected depending on the applied use within the scope of this invention.

Example of the "base plate" which may be used in this invention include glass plates, metal plates and plastics sheets which are resisting to the solvent used for the preparation of the resin solution for forming the protective layer. It is generally preferable that the base plate has a smooth surface. However, the surface of the base plate may have a roughness or irregularity of desired extent (not more than about 20 microns).

The process for preparing the gradient image conversion sheet will now be described.

(1) First Embodiment of the Invention

A gradient pattern is printed on a film serving as a protective layer using an ink of proper color, and then the ink is dried. Thereafter, a coating dispersion for forming a fluorescent layer is coated while using an proper coater, such as a roll coater or a knife coater, followed by drying. In this step, the resin and/or the colorant contained in the ink printed on the film serving as the protective layer is disolved and dispersed in th coating dispersion for forming the fluorescent layer to be finally captured thereinto. As a result, a protective layer and/or a fluorescent layer having a blurred or partially colored areas at the vicinity of the printed pattern are formed. A support made of, for example, paper or plastics sheet is applied on the dried and partially colored fluorescent layer to obtain a gradient image conversion sheet of this invention.

(2) Second Embodiment of the Invention

A gradient pattern is printed on a support made of, for example, paper or plastics sheet, and the thus printed ink is dried. Similarly as in the procedure described in the preceding paragraph (1), a coating dispersion for forming a fluorescent layer is coated and dried. As a result, a fluorescent layer having a blurred or partially colored areas at the vicinity of the printed pattern is formed. By the provision of a film serving as a protective layer over the fluorescent layer, the second embodiment of the gradient image conversion sheet of this invention is obtained.

Meantime, in case where a plastics sheet is used as the protective layer or the protective layer is formed by using a protective layer forming resin solution containing a solvent which does not dissolve the colorant, inter alia the dye, in the printing ink, only the fluorescent layer is colored. However, in case where the protective layer is formed by using a protective layer forming resin solution containing a solvent which dissolves the colorant, inter alia the dye, in the printing ink, not only the fluorescent layer but also the protective layer are colored.

(3) Third Embodiment of the Invention

Following to the procedure as described in paragraph (1), a coating dispersion for forming a fluorescent layer is coated on a support made of, for example, paper or plastics material, followed by drying of the ink. A protective layer forming resin solution is coated on the fluorescent layer printed with the pattern, while using a coater such as a roll coater or a knife coater, followed by drying the thus coated resin solution. In this step, the resin and/or the colorant in the printed ink on the fluorescent layer is dissolved by the solvent contained in the resin solution to be dispersed or bled in the fluorescent layer and the resin solution for forming the protective layer. As a result, a fluorescent layer and a protective layer each having blurred or partially colored areas at the vicinity of the printed pattern are formed to obtain a gradient image conversion sheet of the invention.

(4) Fourth Embodiment of the Invention

A gradient pattern is printed with a dye ink of proper color on a base plate, and the thus printed ink was dried. Using a coater, such as a roll coater or a knife coater, a protective layer forming resin solution was coated and then dried. In this step, the resin and/or colarant in the ink printed on the base plate are dispersed or bled in to the resin solution. As a result, a protective layer having blurred and partially colored areas in the vicinity of the printed pattern is formed. Thereafter, a predetermined amount of a coating dispersion for forming a fluorescent layer was coated using a coater, such as a roll coater or a knife coater, followed by drying. By applying a support made of, for example, paper or plastics material on the thus formed fluorescent layer, a gradient image conversion sheet of the invention is obtained.

In an alternative process, a coating dispersion for forming a fuorescent layer is coated on a support layer using a coater, such as a roll coater or a knife coater, followed by drying, to form a fluorescent layer. The support layer carrying the thus formed fluorescent layer is applied with a protective layer having blurred and partially colored areas in the vicinity of the printed pattern to obtain a gradient image conversion sheet of this invention.

Meanwhile, the protective layer formed on the base plate may be peeled off from the base plate at any selected time or stage. For example, it may be peeled off prior to the formation of the fluorescent layer on the protective layer, or may be peeled off after the fluorescent layer and the support layer have been formed on the protective layer.

In the processes as described in paragraphs (1) to (4), there are a case where all components of the gradient pattern printing ink are bled, a case where only the colorant is bled, and only the resinous ingredient of the ink is bled and the insoluble colorant is entrained by the thus bleeding resinous ingredient to be dispersed under the action of a solvent contained either in the coating dispersion for forming the fluorescent layer or in the protective layer forming resin solution. In either one of the cases, upon migration of the colorant in the gradient pattern printing ink, which has been previously printed, into the fluorescent layer and/or the protective layer, the fluorescent layer and/or the protective layer are formed with blurred and partially colored areas in the vicinity of the printed gradient pattern.

EXAMPLE OF THE INVENTION

The present invention will now be described with reference to specific Examples thereof and Comparative Examples.

EXAMPLE 1

On a protective film made of a 9 micron thick polyethylene terephthalate and applied on a smooth base plate, printed was an ink having the following composition through a silk screen plate having a 300 meshes screen of strip form, the screen strip having a length of 30 cm and a width of 8 cm, of which the 3 cm for each of marginal areas at both edges were graded from 100% to 0%, with the dots size being 60 lines. Thereafter, a coating dispersion of a phosphor having the following composition was coated, dried, and then peeled off from the base plate to prepare a fluorescent sheet in which the fluorescent material was coated using a knife coater in an amount of 50 mg/cm$^2$. The thus prepared sheet was applied on a 240 micron thick PET base by hot pressing to obtain a gradient radiation image conversion sheet of this invention. The film density curve of a film was inspected through the X-ray photography. The result is shown in FIG. 1. As shown, the gradation area or portion is shown by a smooth gradient curve to reveal that the dots have been blurred evenly.

| Composition of Ink: | |
|---|---|
| Nitrocellulose | 40 g |
| DOP | 20 g |
| Cyclohexanone | 200 g |
| Benzidine Yellow | 0.6 g |
| **Composition of Coating Dispersion of Phosphor:** | |
| $CaWO_4$ | 100 g |
| Nitrocellulose | 7 g |
| DOP | 3 g |
| Butyl Acetate | 90 g |

COMPARATIVE EXAMPLE 1

Figure 2:
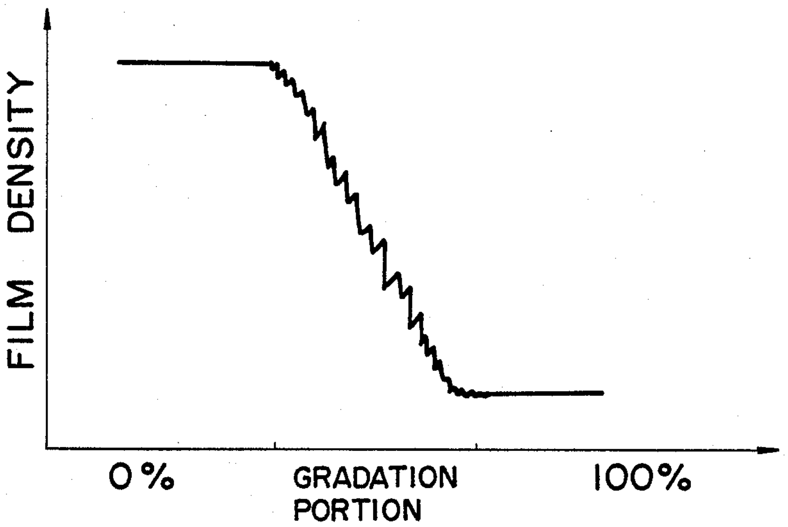
FIG. 2 is a similar graphic representation of an X-ray film density obtained by the use of a gradient image conversion sheet other than those prepared by the present invention.

Generally following to the procedure as described in Example 1, except in that a ink which was not dissolved in the coating dispersion of phosphor and had the following composition was used, a gradient radiation image conversion sheet was prepared and the X-ray film density curve thereof was plotted similarly as in Example 1. The result is shown in FIG. 2. As shown in FIG. 2, the gradient portion of the curve is of zig-zag shape to show that dots have been formed also on the photographed film.

| Composition of Ink: | |
|---|---|
| Cellulose Acetate | 12 g |
| DOP | 1 g |
| Acetone | 87 g |
| Benzidine Yellow | 0.3 g |

EXAMPLE 2

On a protective film made of a 9 micron thick acetylcellulose and applied on a smooth base plate, printed was an ink having the following composition through a silk screen plate having a 300 mesh screen of strip form, the screen strip having a length of 30 cm and a width of 8 cm, of which the 3 cm for each of marginal regions at both edges were graded from 100% to 0%, with the dots size being 60 lines. Thereafter, a coating dispersion of a phosphor having the following composition was coated, dried, and then peeled off from the base plate. The solvent used for the preparation of the coating dispersion of the phosphor was butyl acetate which did not dissolve the cellulose acetate (acetyl cellulose) contained in the solution as a resinous ingredient, but disolved the coloring dye (Diaresin-Yellow C). The thus prepared fluorescent sheet contained the fluorescent material in an amount of 50 mg/cm$^2$. The thus prepared sheet was applied on a 240 micron thick PET base by hot pressing to obtain a gradient radiation image conversion sheet of this invention. The film density curve of a film was inspected through the X-ray photography. The graded portion give a smooth gradient curve similar to the curve shown in FIG. 1 to reveal that the dots have been blurred evenly.

| Composition of Ink: | |
|---|---|
| Cellose Acetate | 12 g |
| DOP | 1 g |
| Cyclohexane | 87 g |
| Diaresin Yellow C (Produced by Mitsubishi Chemical Industried Ltd.) | 0.6 g |
| **Composition of Coating Dispersion of Phosphor:** | |
| $CaWO_4$ | 100 g |
| Nitrocellulose | 7 g |
| DOP | 3 g |
| Butyl Acetate | 90 g |

COMPARATIVE EXAMPLE 2

Generally following to the procedure as described in Example 2, except in that a pigment ink composition, as set forth below, which was not dissolved in the coating dispersion of the phosphor was used to prepare an image conversion sheet. The X-ray film density curve thereof was obtained similarly as in Example 2. The gradient portion is of zig-zag shape similar to the curve shown in FIG. 2 to show that dots are formed also on the photographed film.

| Composition of Ink: | |
|---|---|
| Cellulose Acetate | 12 g |
| DOP | 1 g |
| Cyclohexane | 87 g |
| Benzidine Yellow | 0.1 g |

EXAMPLE 3

An ink having the composition as set forth below was coated on a 240 micron thick PET base, similarly as in Example 1. On the other hand, prepared was a coating dispersion for forming a fluorescent layer having the composition as set forth below. A fluorescent layer was formed by applying the coating dispersion on the base, and then a resin solution for forming a protective layer, having the composition as set forth below, was over-coated on the fluorescent layer, followed by drying, whereby a gradient radiation image conversion sheet of the invention was prepared. The X-ray film density curve obtained in relation to the sheet of this Example had a smoothly gradation or graded portion similar to the curve shown in FIG. 1.

| | |
|---|---|
| Composition of Ink: | |
| Nitrocellulose | 40 g |
| DOP | 20 g |
| Butyl Acetate | 200 g |
| Benzidine Yellow | 0.1 g |
| Composition of Coating Dispersion of Phosphor: | |
| $CaWO_4$ | 100 g |
| Nitrocellulose | 7 g |
| DOP | 3 g |
| Butyl Acetate | 90 g |
| Composition of Resin Solution for Protection Layer: | |
| Cellulose Acetate | 12 g |
| DOP | 1 g |
| Acetone | 87 g |

COMPARATIVE EXAMPLE 3

Generally following to the procedure as described in Example 3, except in that the used ink had the composition as set forth below, an image conversion sheet. The X-ray film density curve of the sheet of this Comparative Example had a zig-zag shape of gradation portion similar to the curve shown in FIG. 2.

| Composition of Ink: | |
|---|---|
| Urethane Resins | |
| NIPPOLLAN 5120 | 50 g |
| CORONATE HL | 5 g |
| MEK | 50 g |
| Benzidine Yellow | 10 g |

EXAMPLE 4

A dye ink having the composition as set forth below was coated on a 240 micron thick PET base, generally similarly as in Example 2. Then, generally following to the procedure as described in Example 2, a fluorescent layer was formed by coating a dispersion of a phosphor, the dispersion containing butyl acetate which did not dissolve cellulose acetate contained as the resinous ingredient of the dye ink but dissolved the coloring dye (Diaresin Yellow C). On the thus formed fluorescent layer, a protective resin solution having the composition as set forth below was coated using a knife coater, followed by drying, to prepare a gradient image conversion sheet of the invention. The X-ray film density curve obtained in relation to the sheet of this Example had a smoothly gradation or graded portion similar to the curve shown in FIG. 1.

| | |
|---|---|
| Composition of Dye Ink: | |
| Cellulose Acetate | 12 g |
| DOP | 1 g |
| Cyclohexane | 87 g |
| Diaresin Yellow C | 0.3 g |
| Composition of Coating Dispersion of Phosphor: | |
| $CaWO_4$ | 100 g |
| Nitrocellulose | 7 g |
| DOP | 3 g |
| Butyl Acetate | 90 g |
| Composition of Resin Solution for Protection Layer: | |
| Cellulose Acetate | 12 g |
| DOP | 1 g |
| Acetone | 87 g |

COMPARATIVE EXAMPLE 4

Generally following to the procedure as described in Example 4, except in that the used ink was a pigment ink and had the composition as set froth below, an image conversion sheet was prepared. The X-ray film density curve of the sheet of this Comparative Example had a zig-zag shaped gradation portion similar to the curve shown in FIG. 2.

| Composition of Pigment Ink: | |
|---|---|
| Cellulose Acetate | 12 g |
| DOP | 1 g |
| Cyclohexane | 87 g |
| Benzidine Yellow | 0.1 g |

EXAMPLE 5

A coating solution for forming a fluorescent layer and having the composition as set forth below was coated on a 240 micron thick PET base using a knife coater and then dried. The thus formed fluorescent layer was printed with an ink having a composition as set forth below while using the same silk screen plate as used in Example 1.

The print formed on the fluorescent layer was covered by a protective layer, by coating a resin solution having a composition as set forth below, followed by drying, to prepare a gradient radiation image conversion sheet of the invention. The X-ray film density curve obtained in relation to the sheet of this Example had a smoothly gradation or graded portion similar to the curve shown on FIG. 1.

| | |
|---|---|
| Composition of Ink: | |
| Cellulose Acetate | 12 g |
| DOP | 1 g |
| Acetone | 87 g |
| Benzidine Yellow | 0.3 g |
| Composition of Coating Dispersion of Phosphor: | |
| $CaWO_4$ | 300 g |
| Urethane Resin | |
| NIPPOLLAN 5120 | 20 g |
| CORONATE HL | 2 g |
| (Produced by Nippon Polyurethane Co., Ltd.) | |
| MEK | 70 g |
| Resin Solution for Protection Layer: | |
| Cellulose Acetate | 6 g |
| DOP | 0.5 g |
| Acetone | 94 g |

COMPARATIVE EXAMPLE 5

Generally following to the procedure as described in Example 5, except in that the used ink had the composition as set forth below, an image conversion sheet was prepared. The X-ray film density curve of the sheet of this Comparative Example had a zig-zag shaped gradation portion similar to the curve shown in FIG. 2.

| Composition of Ink: | |
|---|---|
| Urethane Resin | |
| NIPPOLLAN 5120 | 50 g |
| CORONATE HL | 5 g |
| MEK | 50 g |
| Benzidine Yellow | 0.3 g |

EXAMPLE 6

A coating dispersion for forming a fluorescent layer and having the composition as set forth below was coated on a 240 micron thick PET base using a knife coater and then dried. The thus formed fluorescent layer was printed with a dye ink having a composition as set forth below while using the same silk screen plate as used in Example 2.

On the other hand, a resin solution for a protective layer was prepared by using, as the solvent, butyl acetate which did not dissolve cellulose acetate serving as the resinous ingredient of the dye ink but dissolved the coloring dye (Diaresin Yellow C). The resin solution was coated and dried to form a gradient radiation image conversion sheet of the invention. The X-ray film density curve obtained in relation to the sheet of this Example had a smooth gradation or graded portion similar to the curve shown in FIG. 1.

| | |
|---|---|
| Composition of Dye Ink: | |
| Cellulose Acetate | 12 g |
| DOP | 1 g |
| Cyclohexane | 87 g |
| Diaresin Yellow C | 0.3 g |
| Composition of Coating Dispersion of Phosphor: | |
| $CaWO_4$ | 100 g |
| Nitrocellulose | 7 g |
| DOP | 3 g |
| Butyl Acetate | 90 g |
| Resin Solution for Protection Layer: | |
| Cellulose Acetate Butylate | 6 g |
| DOP | 0.5 g |
| Butyl Acetate | 94 g |

COMPARATIVE EXMAPLE 6

Generally following to the procedure as described in Example 6, except in that the used ink was a pigment ink and had the compositon as set forth below, an image conversion sheet was prepared. The X-ray film density curve of the sheet of this Comparative Example had a zig-zag shaped gradation portion similar to the curve shown in FIG. 2.

| Composition of Pigment Ink: | |
|---|---|
| Cellulose Acetate | 12 g |
| DOP | 1 g |
| Cyclohexane | 87 g |
| Benzidine Yellow | 0.1 g |

EXAMPLE 7

On a protective film made of a 9 micron thick polyethylene terephthalate and applied on a smooth base plate, printed was an ink having the following composition through a silk screen plate having a 300 meshes screen of strip form, the screen strip having a length of 30 cm and a width of 8 cm, of which the 3 cm for each of marginal areas at both edges are graded from 100% to 0% with the dots size being 60 lines. Thereafter, a protective layer forming resin solution having the following composition was coated using a knife coater and dried. The sheet was then peeled off from the base plate to prepare a fluorescent sheet in which the fluorescent material was contained in an amount of 50 mg/cm$^2$. The thus prepared sheet was applied on a 240 micron thick PET base by hot pressing to obtain a gradient radiation image conversion sheet of this invention. The film density curve of a film was inspected through the X-ray photography. The graded portion give a smooth gradient curve similar to the curve shown in FIG. 1 to reveal that the dots have been blurred evenly.

| | |
|---|---|
| Composition of Ink: | |
| Cellulose Acetate | 12 g |
| DOP | 1 g |
| Acetone | 87 g |
| Benzidine Yellow | 0.3 g |
| Composition of Resin Solution for Protection Layer: | |
| Cellulose Acetate | 12 g |
| DOP | 1 g |
| Acetaone | 87 g |
| Composition of Coating Dispersion of Phosphor: | |
| $CaWO_4$ | 100 g |
| Nitrocellulose | 7 g |
| DOP | 3 g |
| Butyl Acetate | 90 g |

COMPARATIVE EXAMPLE 7

Generally following to the procedure as described in Example 7, except in that an ink which was not been dissolved in the resin solution for the protective layer and had the following composition was used, a gradient image conversion sheet was prepared. The X-ray film density curve thereof was plotted, and the gradient portion is of zig-zag shape similar to the curve shown in FIG. 2 to show that dots are formed also on the photographed film.

| Composition of Ink: | |
|---|---|
| Urethane Resin | |
| NIPPOLLAN 5120 | 20 g |
| CORONATE HL | 2 g |
| (Produced by Nippon Polyurethane Co., Ltd.) | |
| MEK | 70 g |
| Benzidine Yellow | 0.3 g |

EXAMPLE 8

A dye ink having the following composition was printed on a 250 micron thick polyethylene terephthalate sheet having a smooth surface, similarly as in Example 2. Then, a resin solution for a protective layer was coated using a knife coater and dried to prepare a protective layer film. The resin solution contained butyl acetate which did not dissolve cellulose acetate contained in the dye ink as the resinous ingredient but dissolved the dye (Diaresin Yellow C) contained in the dye ink as a colorant. A gradient image conversion sheet of this invention was prepared by applying the protective layer film with a fluorescent sheet which was prepared by coating a coating dispersion of phosphor having the following composition on a 240 micron thick PET base using a knife coater, followed by drying. The X-ray film density curve of the thus prepared sheet had a smooth gradation portion similar to the curve shown in FIG. 1.

| | |
|---|---|
| Composition of Dye Ink: | |
| Cellulose Acetate | 12 g |
| DOP | 1 g |
| Cyclohexane | 87 g |
| Diaresin Yellow C | 0.1 g |
| Composition of Resin Solution for Protection Layer: | |
| Cellulose Acetate butylate | 6 g |
| DOP | 0.5 g |
| Butyl Acetate | 94 g |
| Composition of Coating Solution of Fluorescent Material: | |
| $CaWO_4$ | 100 g |
| Nitrocellulose | 7 g |
| DOP | 3 g |

COMPARATIVE EXAMPLE 8

Generally following to the procedure as described in Example 8, except in that a pigment ink having the following composition was used, a gradient image conversion sheet was prepared and an X-ray film density curve thereof was plotted. The X-ray film density curve of the sheet had a zig-zag shaped gradation portion similar to the curve shown in FIG. 2.

| Composition of Ink: | |
|---|---|
| Cellulose Acetate | 12 g |
| DOP | 1 g |
| Cyclohexane | 87 g |
| Benzidine Yellow | 0.1 g |

What is claimed is:

1. A gradient radiation image conversion sheet, comprising:
   - a protective layer carrying a gradient pattern printed with a gradient pattern printing ink containing a resin or colorant,
   - a fluorescent layer formed by applying on said protective layer with a coating dispersion of a phosphor, said coating dispersion containing, in addition to said phosphor, a solvent for at least one of said resin or said colorant in said ink, so that said resin or said colorant are dispersed or bled into said protective layer or said coating dispersion of said phosphor, and
   - a support layer disposed on said fluorescent layer, whereby the transmissions of said protective layer or said fluorescent layer are partially changed and the dots of the print of said gradient pattern and the border between the printed area and the unprinted area are blurred.

2. The gradient radiation image conversion sheet of claim 1 wherein the resin contained in the gradient patterns printing ink is at least one member selected from the group consisting of rosin, shellac, copal, dammar, gilsonite, setting rosin, maleic resins, fumarate resins, phenol resins, xylene resins, ketone resins, petroleum resins, terpentine resins, chlorinated rubbers, alkyd resins, polyamide resins, acrylic resins, polyvinyl chloride, polyvinyl chlorideacetate, nitrocellulose, acetylcellulose and cellulose acetate butyrate.

3. The gradient radiation image conversion sheet of claim 1 wherein the solvent contained in the coating dispersion of the phosphor is at least one member selected from the group consisting of mineral spirit, petroleum naphtha, toluene, xylene, ethyl alcohol, isopropyl alcohol, butyl alcohol acetone, diisobutyl ketone, diethyl ketone, methyl ethyl ketone, acetate esters, butylate ester, isopropyl ether, ethyl ether and cellosolve diethl.

4. A gradient radiation image conversion sheet, comprising:
   - a support layer carrying a gradient pattern printed with a gradient pattern printing ink containing a resin or colorant,
   - a fluorescent layer formed by applying on said support layer with a coating dispersion of a phosphor, said coating dispersion containing, in addition to said phosphor, a solvent for at least at one of said resin or colorant in said ink so that said resin or said colorant are dispersed or bled into said coating dispersion of said phosphor, and
   - a protective layer disposed on said fluorescent layer, whereby the transmissions of said protective layer or said fluorescent layer are partially changed and the dots of the print of said gradient pattern and the border between the printed area and the unprinted area are blurred.

5. The gradient radiation image conversion sheet of claim 4 wherein the resin contained in the gradient patterns printing ink is at least one member selected from the group consisting of rosin, shellac, copal, dammar, gilsonite, setting rosin, maleic resins, fumarate resins, phenol resins, xylene resins, ketone resins, petroleum resins, terpentine resins, chlorinated rubbers, alkyd resins, polyamide resins, arcylic resins, polyvinyl chloride, polyvinyl chloride-acetate, nitrocellulose, acetylcellulose and cellulose acetate butyrate.

6. The gradient radiation image conversion sheet of claim 4 wherein the solvent contained in the coating dispersion of the phosphor is at least one member selected from the group consisting of mineral spirit, petroleum naphtha, toulene, xylene, ethyl alcohol, iospropyl alcohol, butyl alcohol, acetone, diisobutyl ketone, diethyl ketone, methyl ethyl ketone, acetate esters, butylate ester, isopropyl ether, ethyl ether and cellosolve diethl.

7. A gradient radiation image conversion sheet, comprising:
   - a support layer,
   - a fluorescent layer disposed on said support layer, said fluorescent layer carrying a gradient pattern printed with a gradient pattern printing ink containing a resin or a colorant, and
   - a protective layer formed by applying on said fluorescent layer with resin solution containing, a solvent for at least one of said resin or said colorant in said ink and a protective layer forming resin, so said resin or said colorant are dispersed or bled into said fluorescent layer or said coating dispersion whereby the transmissions of said protective layer or said fluorescent layer are partially changed and the dots of the print of said gradient pattern and the border between the printed area and the unprinted area are blurred.

8. The gradient radiation image conversion sheet of claim 7 wherein the resin contained in the gradient pattern forming ink is at least one member selected from the group consisting of rosin, shellac, copal, dammar, gilsonite, setting rosin, maleic resins, fumarate resins, phenol resins, xylene resins, ketone resins, petroleum resins, terpentine resins, chlorinated rubbers, alkyd resins, polyamide resins, acrylic resins, polyvinyl chloride, polyvinyl chloride-acetate, nitrocellulose, acetylcellulose and cellulose acetate butyrate.

9. The gradient radiation image conversion sheet of claim 7 wherein the solvent contained in the resin solution is at least one member selected from the group consisting of mineral spirit, petroleum naphtha, toluene, xylene, ethyl alcohol, isopropyl alcohol, butyl alcohol, acetone, diisobutyl ketone, diethyl ketone, methyl ethyl ketone, acetate esters, butylate ester, isopropyl ether, ethyl ether and cellosolve diethl.

10. A gradient radiation image conversion sheet, comprising:

a protective layer formed by applying on a base plate, said base plate carrying a gradient pattern printed with a gradient pattern printing ink containing a resin or colorant, with a resin solution containing a protective layer forming resin and a solvent for at least one of said resin or said colorant in said ink, so that said resin or said colorant are dispersed or bled into said coating dispersion, a fluorescent layer disposed on said protective layer, and a support layer disposed on said fluorescent layer, whereby the transmissions of said protective layer or said fluorescent layer are partially changed and the dots of the print of said gradient pattern and the border between the printed area and the unprinted area is blurred.

11. The gradient radiation image conversion sheet of claim 10 wherein the resin contained in the gradient patterns printing ink is at least one member selected from the group consisting of rosin, shellac, copal, dammar, gilsonite, setting rosin, maleic resins, fumarate resins, phenol resins, xylene resins, ketone resins, petroleum resins, terpentine resins, chlorinated rubbers, alkyd resins, polyamide resins, acrylic resins, polyvinyl chloride, polyvinyl chlorideacetate, nitrocellulose, acetylcellulose and cellulose acetate butyrate.

12. The gradient radiation image conversion sheet of claim 10 wherein the solvent contained in the resin solution is at least one member selected from the group consisting of mineral spirit, petroleum naphtha, toluene, xylene, ethyl alcohol, isopropyl alcohol, butyl alcohol, acetone, diisobutyl ketone, diethyl ketone, methyl ethyl ketone, acetate esters, butylate ester, isopropyl ether, ethyl ether and cellosolve diethl.

* * * * *